United States Patent [19]

Shahinian, Jr.

[11] Patent Number: 5,610,184

[45] Date of Patent: Mar. 11, 1997

[54] METHOD FOR SUSTAINED AND EXTENDED CORNEAL ANALGESIA

[76] Inventor: Lee Shahinian, Jr., 1506 Country Club Dr., Los Altos, Calif. 94024

[21] Appl. No.: 415,184

[22] Filed: Apr. 3, 1995

Related U.S. Application Data

[63] Continuation-in-part of Ser. No. 183,186, filed as PCT/US95/00564, Jan. 13, 1995, abandoned.
[51] Int. Cl.$^6$ .................................................. A61K 31/24
[52] U.S. Cl. .......................................... 514/540; 514/912
[58] Field of Search ..................................... 514/540, 563, 514/912

[56] References Cited

U.S. PATENT DOCUMENTS 5,411,738  5/1995  Hind ......................................... 424/445

OTHER PUBLICATIONS

Paul M. H. Cherry, et al., The Treatment of Pain Following Photorefractive Keratectomy, *Supplement to Journal of Refractive and Corneal Surgery*, vol. 10, pp. 222–225, Mar./Apr. 1994.

Verna S., et al., Pain Control After PRK: Do Topical Anesthetics Have a Role?, *American Academy of Ophthalmology*, Annual Meeting, p. 102, Nov. 1995.

*Primary Examiner*—Zohreh Fay
*Attorney, Agent, or Firm*—Hana Verny

[57] ABSTRACT

A method for sustained and extended corneal analgesia by repeated administration of ophthalmic analgesic solutions or preparations containing ultralow nontoxic subanesthetic concentrations of local anesthetic agents. A method for corneal analgesia has a fast onset of pain relief and extended duration of the corneal analgesia for several months without accompanying toxic symptoms by administering to a patient an ophthalmic analgesic solution containing a local anesthetic agent in ultralow concentration between about 0.001% and about 0.05%.

32 Claims, No Drawings

METHOD FOR SUSTAINED AND EXTENDED CORNEAL ANALGESIA

This is a continuation-in-part application of application Ser. No. 08/183,186 filed on Jan. 14, 1994 now abandoned, and the PCT application PCT/US95/00564 filed on Jan. 13, 1995.

BACKGROUND OF THE INVENTION

1. Field of Invention

The current invention concerns a method for sustained and extended corneal analgesia by repeated administration of ophthalmic analgesic solutions or analgesic preparations containing ultralow nontoxic subanesthetic concentrations of local anesthetic agents. In particular, the invention concerns a method for corneal analgesia having a fast onset of pain relief and extended duration of the corneal analgesia for several months without accompanying toxic symptoms by administering to a patient an ophthalmic analgesic solution or analgesic preparation containing a local anesthetic agent in ultralow concentration between about 0.001% and about 0.05%.

2. Background Art and Related Art Disclosures

Trauma to the eye, particularly corneal injury and abrasion, tends to be excruciatingly painful. While many anesthetic agents such as proparacaine, cocaine, procaine, tetracaine, hexylcaine, bupivacaine, lidocaine, benoxinate, mepivacaine, prilocaine and etidocaine, to name a few, are well known to attain temporary anesthesia and suppression of pain, concentrations of these agents needed to achieve corneal anesthesia are between 0.25% and 4%. At these concentrations, these agents can only be administered for a very short period of time necessary to achieve local anesthesia and permit performance of ophthalmic procedures such as examination of a painful eye, measurement of intraocular pressure, gonioscopic examination, removal of foreign bodies and sutures from the cornea, diagnostic conjunctival and corneal scrapings, radial keratotomy, and other surgical procedures. The onset of the anesthesia is very rapid, typically under 15 seconds, and typically lasts for about 10–30 minutes. Unfortunately, application of local anesthetics to the cornea at these concentrations causes the development of temporary superficial corneal epithelial lesions. Upon repeated application for prolonged anesthesia, these lesions progress to extensive erosions of the corneal epithelium and grayish infiltrates of the corneal stroma which can lead to permanent scarring and loss of vision. Prolonged application of local anesthetics is further associated with delayed corneal reepithelialization after wounding, altered lacrimation and tear film stability, corneal swelling, and disruption of epithelial cell mitosis and migration.

It is therefore clear that the use of local anesthetics in their normal and intended manner is limited to short-term anesthesia and cannot be safely utilized for sustained decrease or elimination of pain over several hours or days.

Anesthesia, which is a partial or total loss of the sense of pain, temperature, and touch, is very different from analgesia, a state in which the individual does not feel pain but feels other sensations, such as touch or temperature.

Sustained ophthalmic analgesia is very difficult to achieve. This is particularly true with respect to corneal analgesia. The cornea is the clear dome-shaped window in the front of the eye. The cornea serves two functions. First, it forms the front part of the eye's outer wall and thus protects structures inside the eye. Second, with its curved shape, the cornea acts like a camera lens to transmit light and focus images on the retina at the back of the eye. The epithelium (outermost layer) of the cornea is heavily innervated. Therefore, the cornea is very sensitive, and any damage to the surface epithelium can cause severe pain.

A common cause of such pain is a break in the corneal epithelium. Such epithelial defects can be caused by corneal drying, infection and inflammation which damage epithelial cells, by corneal dystrophies with loosely adherent epithelium, or by mechanical removal of the corneal epithelium in traumatic abrasions or surgical procedures. In most cases, the pain persists until the epithelial defect has healed.

At present, in order to provide immediate but short-term alleviation of the severe pain experienced by patients suffering from corneal epithelial defects, commercially available local anesthetics can be applied topically to the eye, providing rapid onset of short-acting corneal anesthesia. Two commonly used topical anesthetics are proparacaine in a concentration of 0.5% (5,000 µg/ml) and tetracaine 0.5% (5,000 µg/ml). Lidocaine 4% (40,000 µg/ml) is also occasionally used.

While short-term relief from pain accompanies the application of these anesthetics, there are conditions of the cornea where such short term relief from pain is not sufficient and where prolonged analgesia is necessary and desirable. This is especially true for relief of pain associated with corneal epithelial defects. In these instances, the toxicity associated with repeated use of topical anesthetics for achieving sustained corneal analgesia has been well documented. In *Ocular Pharmacology*, Fifth Edition, C. V. Mosby, St. Louis, pages 75–76 (1983), the repeated use of anesthetic concentrations of topical anesthetics was found to be detrimental to the cornea, and the article states that the repeated use of anesthetics is prohibited because of their toxicity. Thus, the toxicity of these anesthetic agents precludes their repeated use for prolonged corneal analgesia. At this time, therefore, acceptable methods for long-term relief of corneal pain are limited to patching and oral analgesics.

Patching provides partial pain relief in some patients by reducing eyelid movement over the corneal surface and limiting exposure to the outside environment. However, patching has many disadvantages. It is difficult for the patient to reapply the patch properly when it becomes loose or soiled. Patching restricts the frequent use of topical medications. It raises the temperature of the eye surface and thus supports the growth of microorganisms. Finally, many patients are uncomfortable with an eye patched. While patching with a bandage soft contact lens may overcome some of these problems, patching provides incomplete pain relief in most patients and is no substitute for sustained analgesia in patients suffering from corneal epithelial defects, where the pain can persist for several days to several weeks or months.

Oral agents are reasonably effective in reducing corneal pain. However, onset of action is gradual and slow rather than immediate. Doses adequate for corneal analgesia are high and usually cause significant generalized sedation, occasionally accompanied by nausea and vomiting and rarely by life-threatening allergic reactions.

It would therefore be highly desirable and advantageous to have available a method for treatment of acute and chronic corneal pain without exposing a patient to the undesirable side effects of currently available oral analgesics, to the inadequate analgesia and inconvenience associated with patching, or to the toxic effects of repeated doses of currently available concentrations of topical anesthetics.

It is therefore the primary object of this invention to provide a method for achieving sustained and extended corneal analgesia by administration of ultralow concentrations of local anesthetic agents formulated in topical ophthalmic analgesic solutions or ophthalmic analgesic preparations.

SUMMARY

One aspect of the current invention is a method for sustained corneal analgesia by topical administration of subanesthetic concentrations of local anesthetics.

Another aspect of the current invention is a method for relief of corneal pain by administering topically to the cornea an ophthalmic analgesic solution or preparation containing an ultralow concentration of local anesthetic sufficient to assert an analgesic effect.

Still another aspect of the current invention is a method for alleviating corneal pain by administration of an ophthalmic analgesic solution or preparation containing a local anesthetic in concentrations from about 0.001% to about 0.05%.

Still yet another aspect of the current invention is a method for safely alleviating corneal pain by administration of an ophthalmic analgesic solution or preparation containing an ultralow concentration of local anesthetic on an as needed basis decided by the patient, as often and for as long as necessary.

Still yet another aspect of the current invention is a topical ophthalmic analgesic solution consisting essentially of about 0.001%–0.05% local anesthetic selected from the group consisting of proparacaine, tetracaine and lidocaine dissolved in an artificial tear solution or other solution physiologically compatible with the eye, optionally containing pharmaceutically acceptable excipients, additives and preservatives.

Still yet another aspect of the current invention is a method for corneal analgesia comprising steps:

(a) preparing an ophthalmic analgesic solution containing from about 0.001% to about 0.05% of local anesthetic;

(b) administering 1 drop of the solution of step (a) to a patient requiring corneal analgesia;

(c) repeating the administration of the ophthalmic solution of step (b) on an as needed basis for as often and as long as necessary.

DEFINITIONS

As used herein:

"Local anesthetics" means any anesthetics which can be administered locally. Examples of such anesthetics are proparacaine, lidocaine, tetracaine, procaine, cocaine, hexylcaine, bupivacaine, benoxinate, mepivacaine, prilocaine, chloroprocaine, propoxycaine, dyclonine, pramoxine, benzocaine, dibucaine, and etidocaine.

"Ultralow concentration" means a concentration from about 0.001% to about 0.05%, that is, from about 10 μg to about 500 μg per milliliter of ophthalmic solution or artificial tears.

"Ophthalmic analgesic solution" means artificial tears or other physiologically compatible solution containing an ultralow concentration of local anesthetic.

"Dose" means 1 drop of the ophthalmic analgesic solution.

"Physiologically compatible solution" means an ophthalmic solution which contains pharmaceutically acceptable excipients, additives or preservatives dissolved in purified water and which is physiologically compatible with the eye surface.

"Ophthalmic analgesic preparation" means any cream, gel, sustained release vehicle or ointment containing an ultralow concentration of local anesthetic, which preparation is suitable for topical ophthalmic use.

"Subanesthetic concentration" means ultralow concentration of local anesthetic which produces an analgesic effect when applied topically to the cornea where analgesia is achieved without significant loss of corneal touch sensation.

DETAILED DESCRIPTION OF THE INVENTION

The current invention concerns a method for extended and sustained corneal analgesia by administration of subanesthetic ultralow concentrations from about 0.001% to about 0.05% of local anesthetic as an ophthalmic analgesic solution or preparation.

Local anesthetics administered topically in their typical manner at concentrations around and above 0.5% show definite toxicity to the cornea and their use is therefore limited to short-term administration. Recently, some animal experiments in vitro and in vivo have indicated that low concentrations of anesthetic agents are not toxic to the cornea. The studies are described in *Am. J. Ophthalmology*, 99:691–696 (1985), and *Investigative Ophthalmology and Visual Science*, 33:3029–3033 (1992).

It has now been surprisingly found that ten (10) to five hundred (500) fold dilutions of the local anesthetics provide extended and sustained analgesia to the injured or diseased human cornea in vivo. This analgesia is achieved without loss of corneal touch sensation, that is, without inducing corneal anesthesia. Additionally, the ultralow concentrations of the local anesthetics achieve analgesia without any toxicity and without interference with healing, and are therefore both highly effective in relieving corneal pain and also safe for long term analgesia.

In practice of the current invention, the ophthalmic analgesic solution is prepared by diluting any local anesthetic such as proparacaine, tetracaine, lidocaine, cocaine, chloroprocaine, propoxycaine, dyclonine, pramoxine, benzocaine, procaine, hexylcaine, bupivacaine, benoxinate, mepivacaine, prilocaine, dibucaine, and etidocaine, preferably proparacaine, lidocaine and tetracaine, commercially available. The anesthetic is diluted about 10 to 500 times in artificial tears solution or other physiologically compatible solution. These physiologically compatible solutions can be made of or additionally contain any pharmaceutically acceptable excipient, additive or preservative such as sodium chloride, potassium chloride, boric acid, sodium borate, sodium bicarbonate, sodium sulfite, sodium acid phosphate, disodium phosphate, sodium citrate, calcium chloride, sodium lactate, magnesium chloride, polyethylene glycol 300 and 400, povidone, carboxymethylcellulose, hydroxypropylmethylcellulose, glycerin, polyvinyl alcohol, Dextran 70, dextrose, polyquaterium 1, benzalkonium chloride, thimerosal, phenylmercuric nitrate, chlorbutanol, sorbic acid, disodium edetate, hydrochloric acid or sodium hydroxide to adjust the pH, and other agents added in concentrations which are non-toxic to the cornea. The local anesthetics and the pharmaceutically acceptable excipients, additives or preservatives are dissolved in sterile distilled or sterile purified water to provide a solution physiologically compatible with the eye. The final concentration of local anesthetic in these new ophthalmic analgesic solutions is thus from about 0.001% to about 0.05%.

Instead of a solution, the ophthalmic analgesic preparation may be in the form of a cream, gel, or ointment, or in a sustained release vehicle delivering from about 0.001% to about 0.05% local anesthetic.

Under normal conditions, the human tear volume averages about 7 µl. The estimated maximum volume of the cul-de-sac is about 30 µl with drainage capacity far exceeding lacrimation rate. The outflow capacity accommodates the sudden large volume resulting from the instillation of an eye drop. Most commercial eye drops range from 30 to 75 µl in volume. However, much in excess of 30 µl is unable to enter the cul-de-sac and is removed by drainage.

In designing an appropriate dosage unit in ophthalmic applications, there seems to be a practical limit or limits to the concept of minimum dosage volume. First, there is difficulty in designing and producing a dropper configuration which will deliver small volumes without overflow. Second, the patient often cannot detect the administration of a very small volume. This lack of sensation is particularly apparent at the 5.0–7.5 µl dose volume range. Therefore, a typical dosage for the ophthalmic solution is 1 drop which contains between 30–70 µl of which approximately only 30 µl can remain in the cul-de-sac.

Typically, in the practice of the current invention, one drop of ophthalmic analgesic solution consisting essentially of about 0.001%–0.05% of a local anesthetic as listed above, dissolved in an artificial tear solution, such as for example, TEARS NATURALE® or TEARS NATURALE FREE® available from Alcon Laboratories, Forth Worth, Tex., or HYPOTEARS® or HYPOTEARS PF®, available from Iolab Corp., Claremont, Calif., or in another solution physiologically compatible with the eye surface, or formulated in other pharmaceutically acceptable vehicles and preparations, is administered repeatedly to a patient's cornea for sustained and extended pain relief.

The analgesic solution or preparation is administered to a patient suffering from corneal epithelial defect, whether of mechanical, inflammatory, infectious or chemical origin, caused by surgery, injury, diagnostic procedure or disease, as 1–3 drops of the solution or an appropriate amount of sustained release vehicle, cream, ointment or gel applied to the eye surface as needed for the relief of pain, such as every 5–30 minutes, every 1–6 hours, twice a day, or more or less frequently on an as needed basis, for as long as needed. A typical regimen is the administration of 1 drop of 0.005% solution, that is, of about 1.5 µg of anesthetic, every 1–4 hours during the first day of the treatment followed by decreasing the number of applications as the epithelial defect heals and the pain subsides. The patient uses a drop of the ophthalmic analgesic solution or other ophthalmic analgesic preparation as often as necessary for the relief of pain. Therefore, the actual frequency of use is usually determined by the patient, and is dependent on the size and severity of the epithelial defect, the rate of healing, and the patient's pain threshold. In general, the selected ophthalmic analgesic solution or preparation contains the lowest anesthetic concentration which consistently provides relief of pain for a patient or a population of patients. Due to its safety because of the ultralow concentration of the anesthetic, the analgesic solution or preparation of this invention can be used as frequently as necessary to control pain.

Ophthalmic analgesic solutions or preparations can be repeatedly and safely applied topically to the eye as often as necessary for as long as several months.

In absolute amounts, the active ingredient, that is, a chosen local anesthetic, is administered in amounts from about 0.30 µg to about 15 µg/per one dose. The dose is calculated as follows. The 0.005% analgesic solution contains 50 µg of local anesthetic per 1 ml of solution. One drop of the commercial ophthalmic solution typically ranges from 30–70 µl, however, since the maximum volume of the cul-de-sac is only 30 µl, only 30 µl of the solution is delivered to the cornea. In 1 ml of the 0.005% solution (50 µg/ml), there are approximately 33 drops. In each drop, therefore, there is about 1.5 µg/drop of anesthetic actually delivered to the cornea. In less concentrated solutions of 0.0025% and 0.001%, the absolute amount of anesthetic delivered to the cornea per one drop of the analgesic solution is about 0.75 µg and 0.30 µg respectively. The concentration of the anesthetic in other ophthalmic analgesic preparations is generally equivalent to that in the ophthalmic analgesic solutions, and the amount of anesthetic administered via the ointment, cream, gel or sustained release vehicle will be generally be similar to that delivered by the solution.

In its broadest aspect, the invention concerns a method for alleviating corneal pain by administration of ophthalmic analgesic solutions or preparations containing local anesthetic agents in a specified range of concentrations, such solutions or preparations to be applied topically in effective doses to the human cornea in vivo to safely provide sustained analgesia when corneal epithelial defects are present.

In three clinical studies performed on patients with corneal epithelial defects, the efficacy and safety of the current method was demonstrated. The administration of 1 drop of ultralow concentration of anesthetic to the eye resulted in almost immediate alleviation of pain. Repeated doses had no detrimental effect on the cornea or on the healing of the corneal epithelial defect.

In these studies, concentrations of administered anesthetic were from about 0.0005% to about 0.05%. In terms of absolute amount of anesthetic administered, as little as 0.15 µg per dose (0.0005%) was found to be somewhat effective analgesic in some cases. Anesthetics administered in amounts from 0.001% to 0.05% were found to be extremely effective as analgesics for alleviation of corneal pain. The results are described in detail in three clinical studies (A, B and C) involving 38 patients (two patients participated in two studies) who used the analgesic solutions of the current invention to alleviate corneal pain associated with corneal abrasion and other corneal epithelial defects.

In the first clinical study (Study A), 5 patients suffering from various epithelial defects were treated with 10–50 times dilutions of a commercial preparation containing 0.5% (5,000 µg/ml) proparacaine. The tested solution contained either 500 µg/ml or 100 µg/ml of proparacaine. The 500 µg/ml solution was used in one patient (Case A1) for alleviation for pain following the removal of the corneal epithelium for treatment of corneal dystrophy. Postoperatively, the patient was given one drop of 0.05% (500 µg/ml) solution every hour while awake for three days. The patient reported good relief of pain. The epithelium healed at a normal rate, and there were no toxic reactions or adverse effects on the cornea observed.

When the same treatment regimen was tried on the second patient (Case A2) and compared with 0.01% (100 µg/ml) solution, it was determined that 0.05% solution did not provide any additional pain relief. Following the treatment with 0.01% analgesic solution, the abrasion of the second patient healed quickly within one day without any observable toxic reaction. Three other patients (Cases A3–5) were treated with 0.01% solutions of proparacaine using a 3 times per day or as needed regimen. One patient (Case A3) with chronic recurrent epithelial defects was treated in this way for 17 days, during which time the pain was completely controlled, there were no signs of toxicity, and healing progressed normally and even seemed to be faster than expected.

Summarizing the results from the first study, in five patients with corneal epithelial defects, solutions of approximately 0.01% and 0.05% proparacaine provided sustained analgesia when applied repeatedly as eye drops. No toxicity or delay in epithelial healing was seen. In one case the medication seemed to facilitate epithelial healing. While 0.05% proparacaine appeared to be well tolerated when used for several days in one patient, it did not appear to provide additional analgesic effect when compared with 0.01% proparacaine in another patient. This study indicated the possibility that even lower concentrations than 0.01% of the anesthetics could provide analgesic effect.

In the second clinical study (Study B), ten patients were treated with even more diluted analgesic solutions. In this series, three local anesthetics, lidocaine, tetracaine and proparacaine, in subanesthetic 0.005%, 0.0025%, 0.001% and 0.0005% dilutions, were tested and compared to artificial tears solutions.

The effective analgesia and lack of corneal epithelial toxicity afforded by the 0.005% solution was dramatically demonstrated in Case B1. The patient suffered from recurrent chronic epithelial defects (filamentary keratitis) of uncertain origin. He had not responded to a variety of topical antibiotics and artificial tears. He was treated with one drop of 0.005% proparacaine solution, that is, with 1.5 µg of proparacaine, every 2 hours while awake. The cornea healed completely within a week, with no sign of drug toxicity. After two weeks, this dose was reduced to every 12 hours and continued for two months with the patient reporting no pain during this time. Since the chronic epithelial defects, previously unresponsive to various medications, had healed while the patient was using the analgesic solution, it was decided to maintain the patient on a low concentration analgesic solution. After 2 months, the patient was switched to a 0.0025% solution. One drop (0.75 µg) of this proparacaine solution was administered every 12 hours as maintenance medication to prevent recurrence of the chronic epithelial defects and associated pain. After four months, the cornea remained healed with no pain or epithelial toxicity, and the 0.0025% solution was reduced to once a day. Corneal sensation (sensitivity to touch) remained intact throughout the four month course of treatment.

In Case B6, a patient with pain and epithelial defects following a surgical procedure to treat a corneal epithelial dystrophy was treated with analgesic solutions containing proparacaine in concentrations 0.0005%, 0.001%, 0.0025%. This treatment was compared to placebo treatment with artificial tears. Slight relief from pain was observed with analgesic solution where the amount of the anesthetic administered to the patient was at least 0.30 µg/drop (0.001%). The analgesic solution containing proparacaine 0.0025% (0.75 µg/drop) provided immediate pain reduction. Placebo and 0.0005% solution gave no pain relief.

Overall, ophthalmic analgesic solution containing 0.005% proparacaine was very effective in reducing or eliminating pain. Solutions containing 0.0025% and 0.001% proparacaine were sufficiently effective and in some patients could be effectively substituted for the stronger 0.005% solution. Analgesic solution containing 0.0005% proparacaine was found somewhat effective.

Ophthalmic analgesic solutions containing tetracaine in 0.0005%, 0.001%, and 0.005% concentrations were studied in one case (B7) of corneal abrasion. A solution containing 0.005% tetracaine was found to be very effective in suppressing the pain. The solution containing 0.001% tetracaine gave partial relief of pain, and 0.0005% tetracaine had no effect on pain.

Ophthalmic analgesic solutions containing lidocaine in 0.0005%, 0.001%, 0.0025% and 0.005% concentrations were studied in two cases (B9 and B10) of mechanical corneal injury. A solution containing 0.0005% lidocaine had no effect on pain. Analgesic solutions with 0.001% lidocaine in one case and 0.005% lidocaine and the other case gave rapid pain relief.

Summarizing the results of the second study, three different local anesthetics were found to be effective analgesics for topical corneal analgesia when administered in subanesthetic concentrations from 0.0005% to 0.01%. Good pain relief was achieved in all instances typically with 0.001% to 0.005% of proparacaine, tetracaine, and lidocaine.

In the third clinical study (Study C), 25 patients suffering from cornea abrasion (C1–C11 and C25), epithelial dystrophy (C12, C13), corneal edema (C14), dry eyes (C15), post-op pterygium (C16, C17), and photorefractive keratectomy (C18–C24) were treated with a variety of ultralow analgesic concentrations of topical anesthetics, as seen in Table 3 and as described in Example 3.

As seen in Table 3 and as evident from the case history for each patient, good pain relief and healing without toxicity was achieved with benoxinate solution at 0.001% concentration in corneal abrasion. Benoxinate 0.0005% concentration was able to achieve a slight or partial pain relief and no dose over 0.05% was necessary to achieve good pain relief in corneal abrasion.

Summarizing the results of the third study, this study confirmed that the local anesthetics benoxinate, bupivacaine, proparacaine and tetracaine are effective topical analgesic agents for injured or diseased cornea when applied in ultralow subanesthetic concentrations. In all instances, there was a good pain relief without any sign of toxicity to the cornea.

Summarizing results obtained in all three studies. In 9 patients suffering from corneal abrasion, proparacaine in concentration from 0.001–0.05% was sufficient to reduce pain and allow healing without any sign of toxicity. In patients suffering from epithelial dystrophy, analgesic dose between 0.01–0.05% provided sustained pain relief, decreased eyelid swelling and conjunctiva redness, and allowed healing with no corneal toxicity. In patients suffering from corneal edema and dry eyes, the proparacaine dose of 0.02% was able to achieve good pain relief without toxicity. In the alleviation of pain in post operative pterygium, proparacaine doses between 0.03 and 0.05% achieved good pain relief, pain reduction, and healing without toxicity. Similarly, following the photorefractive keratectomy laser procedure, proparacaine doses between 0.03%–0.05% reduced pain and allowed healing without toxicity.

Overall, based on the above studies, clinical concentrations of lidocaine, proparacaine, benoxinate, bupivacaine and tetracaine from 0.001% (10 µg/ml) to 0.05% (500 µg/ml), applied as eye drops, are effective in relieving pain caused by corneal epithelial defects. While long-term administration of anesthetic doses of these agent are known to be toxic to the cornea, no clinical toxic effects were observed with repeated application at the subanesthetic concentrations. Utilization of sustained release vehicles for delivery of subanesthetic dosages of the topical anesthetics may achieve sufficient analgesia at even lower concentrations because of continuous release of anesthetic.

In summary, in 38 patients suffering from corneal epithelial defects or injuries, dilute solutions of benoxinate, lidocaine, bupivacaine, proparacaine, and tetracaine provided sustained analgesia when applied repeatedly as eye drops in subanesthetic concentration. No observed delay in epithelial healing was observed. No corneal toxic effects related to the treatment were noted.

Additionally, during the clinical studies A–C, it has been observed that applanation tonometry (measurement of intraocular pressure by touching the eye) could not be performed in patients receiving ultralow concentrations of local anesthetics because the treated cornea was still sensitive to touch. This observation was contrary to the prior observations following the administration of anesthetic dosages (0.5% and above) of the local anesthetics into the eyes, where the cornea became completely insensitive to touch. To further explore this observation, two patients' corneas were treated with proparacaine 0.005%, 0.01%, and 0.05% drops, prior to performing surgical procedures that required topical anesthesia. Corneal touch sensation was tested with a wisp of cotton applied to the cornea after instilling each concentration of proparacaine. Corneal touch sensation was found to be present following administration of all three subanesthetic concentrations. In contrast, when proparacaine in anesthetic concentration (0.5%) was subsequently instilled on the cornea, corneal touch sensation immediately disappeared.

Based on these clinical observations, further studies which are illustrated in Example 4 were performed. From these studies, it has been concluded that when ultralow concentrations of local anesthetic are applied to the cornea, analgesia is achieved without loss of corneal touch sensation, that is, without inducing corneal anesthesia. In other words, subanesthetic concentrations which are at least 10 times lower than anesthetic concentrations of these drugs produce an analgesic but no anesthetic effect when applied topically to the cornea.

At anesthetic concentrations, these drugs are known to cause complete nerve depolarization and to block all transmission. In agreement with this observation, and as seen in Table 4, 0.5% proparacaine depolarized the nerve, blocked all nerve transmission and eliminated corneal sensation.

At subanesthetic concentrations of the topical anesthetic, the nerve was not depolarized, nerve transmission was present and corneal sensation remained. Thus, topical anesthetics administered in subanesthetic concentrations substantially decreased or eliminated the pain but did not eliminate corneal sensation. Consequently, since the cornea was still sensitive to touch, action of the anesthetics was not depolarization of the nerve, observed following the anesthesia, but it was true analgesia which can be physiologically distinguished from anesthesia.

UTILITY

The ophthalmic analgesic solution or preparation and the method of treatment described herein are useful for alleviation of pain of the eye caused by corneal epithelial defects secondary to trauma, drying, infection, inflammation, surgery, corneal dystrophy, or other cause. The method is fast and safe and immediately causes substantial or complete relief of pain. The analgesic solution or preparation contains ultralow concentrations of a local anesthetic, and by repeated applications or continuous release safely provides sustained and extended topical analgesic effect on the cornea. The solution is easily prepared in a sterile form, has practical shelf-life and is easy to administer.

EXAMPLE 1

Clinical Study (A) of Sustained Analgesic Effect of Ultralow Concentrations of Proparacaine This example illustrates clinical experiments and evaluation of five patients suffering from corneal abrasion or chronic epithelial defects.

Proparacaine hydrochloride, known under its trade name ALKANE®, was obtained from Alkane Laboratories as 0.5% ophthalmic solution.

The 0.5% solution of proparacaine (5,000 µg/ml) was diluted about 10:1 to 0.05% or 500 µg/ml, and about 50:1 to 0.01% or 100 µg/ml, with HYPOTEARS®, a commercially available artificial tear preparation from Iolab Corporation. This was done by adding 9 drops and 2 drops of proparacaine (39±7 µl per drop) to separate 3 ml bottles of artificial tears. These dilute proparacaine solutions were used on five patients suffering from epithelial defects.

Case A1

Diagnosis: Surgical Corneal Abrasion for Map Dot Fingerprint Corneal Dystrophy

The patient's corneal epithelium was removed for treatment of a dystrophy, using conventional topical anesthetic.

Postoperatively, one drop of proparacaine 0.05% (500 µg/ml) was applied every hour. Good relief of pain was observed within a few seconds following drop administration. The 5 mm epithelial defect healed in 3 days without evidence of epithelial toxicity, and without the need for patching or oral analgesics.

Case A2

Diagnosis: Traumatic Corneal Abrasion

The patient suffered a linear corneal abrasion from paper cut. One drop of 0.01% (100 µg/ml) proparacaine solution relieved her pain within 15 seconds. Further application of 0.05% (500 µg/ml) proparacaine gave no additional relief. Therefore, she was given proparacaine 0.01% drops to use as needed. She used the drops several times a day and reported that the pain subsided. The abrasion healed within a day.

Case A3

Diagnosis: Filamentary Keratitis

The patient had recurrent chronic epithelial defects of uncertain etiology on the superior half of his left cornea with associated pain. These defects had not healed by application of various combinations of topical antibiotics, steroids, artificial tears, and bandage contact lenses.

The patient was treated with ophthalmic analgesic solution. He had immediate relief of pain and his epithelial defects healed in a few days, using proparacaine 0.01% 3 times per day. After 17 days of treatment, the cornea was still clear, with no sign of toxicity, and drops were discontinued.

Case A4

Diagnosis: Surgical Corneal Abrasion for Map Dot Fingerprint Corneal Dystrophy

The patient's corneal epithelium was removed for treatment of a dystrophy, using conventional topical anesthetic.

Postoperatively, patching was poorly tolerated, and 2 days after surgery the patient had a 5 mm epithelial defect with moderate pain. The eye was treated with proparacaine 0.01% 3 times daily. No pain was reported, and examination 2 days later revealed a healed cornea with no sign of toxicity.

Case A5

Diagnosis: Surgical Corneal Abrasion for Band Keratopathy

The patient's corneal epithelium was removed for treatment of calcific band keratopathy.

The epithelium healed partially with patching over 3 days. Two small epithelial defects remained. Patching was discontinued.

The patient was given proparacaine 0.01% drops to use as needed for pain. The cornea was healed by the return visit 3 days later. The drops had given adequate relief of pain.

TABLE 1

CLINICAL EVALUATION OF ANALGESIC EFFECT OF PROPARACAINE

| CASE | DIAGNOSIS | ANESTHETIC | CONCEN-TRATION | REGIMEN | RESULTS |
|------|-----------|------------|----------------|---------|---------|
| A1 | Abrasion | Proparacaine | 0.05% | 3 days/every hour | Healed<br>Good pain relief |
| A2 | Abrasion | Proparacaine | 0.01%<br>0.05% | 1 day/as needed | Healed<br>Good pain relief with .01% & .05% |
| A3 | Filamentary Keratitis | Proparacaine | 0.01% | 17 days/3 times a day | Healed in 17 days<br>Good pain relief<br>No toxicity |
| A4 | Abrasion | Proparacaine | 0.01% | 2 days/3 times a day | Healed in 2 days<br>Good pain relief |
| A5 | Abrasion | Proparacaine | 0.01% | 3 days/as needed | Healed in 3 days<br>Good pain relief |

In summary, in five patients with corneal epithelial defects, solutions of approximately 0.01% and 0.05% proparacaine provided sustained analgesia when applied repeatedly as eye drops. No toxicity or delay in epithelial healing was seen, and in case A3 the medication possibly facilitated epithelial healing. While 0.05% proparacaine appeared to be well tolerated when used for several days in one patient, it did not appear to provide additional analgesic effect when compared with 0.01% proparacaine in another patient.

EXAMPLE 2

Clinical Study (B) of Sustained Analgesic Effect of Ultralow Concentration of Local Anesthetics This example illustrates clinical experiments and evaluation of ten patients receiving ophthalmic analgesic solutions of various concentrations.

Solutions

Lidocaine hydrochloride was obtained from Abbott Laboratories as 1.0% solution for injection.

Proparacaine hydrochloride, known under its trade name ALCAINE®, was obtained from Alcon Laboratories as 0.5% ophthalmic solution.

Tetracaine hydrochloride was obtained from Iolab Corporation as 0.5% ophthalmic solution.

Using a tuberculin syringe and a 30 g needle to allow accurate dilution with HYPOTEARS®, a commercially available artificial tear preparation from Iolab Corporation, solutions of lidocaine, proparacaine, and tetracaine were prepared at various concentrations. Double dilution techniques were used to make optimum use of the tuberculin syringe calibration. These solutions were given the generic name "Turbotears™", and were designated as follows:

| Turbotears ™ | | |
|---|---|---|
| L1 | Lidocaine 0.005% (50 µg/ml) in artificial tears |
| L2 | Lidocaine 0.0025% (25 µg/ml) in artificial tears |
| L3 | Artificial tears |
| L4 | Lidocaine 0.001% (10 µg/ml) in artificial tears |
| L5 | Lidocaine 0.0005% (5 µg/ml) in artificial tears |
| P1 | Proparacaine 0.005% (50 µg/ml) in artificial tears |
| P2 | Proparacaine 0.0025% (25 µg/ml) in |

-continued

| Turbotears ™ | | |
|---|---|---|
| | artificial tears |
| P3 | Artificial tears |
| P4 | Proparacaine 0.001% (10 µg/ml) in artificial tears |
| P5 | Proparacaine 0.0005% (5 µg/ml) in artificial tears |
| T1 | Tetracaine 0.005% (50 µg/ml) in artificial tears |
| T2 | Tetracaine 0.0025% (25 µg/ml) in artificial tears |
| T3 | Artificial tears |
| T4 | Tetracaine 0.001% (10 µg/ml) in artificial tears |
| T5 | Tetracaine 0.0005% (5 µg/ml) in artificial tears |

The following patients with corneal epithelial defects were treated with Turbotears™ solutions:

Case B1

Diagnosis: Filamentary Keratitis

Case B1 describes treatment of the same patient as described in Case A3, Example 1. The patient had recurrent chronic epithelial defects of uncertain etiology. Symptoms recurred within 2 weeks of discontinuing the treatment described in Study A (Case A3). Subsequently, the patient continued to have recurrent episodes of epithelial breakdown and pain, with variable response to lubricating agents (artificial tears).

After five months of recurrent disease, the patient was restarted on an ophthalmic analgesic solution. Turbotears™ solution P1 containing 0.005% proparacaine was initially used every 2–3 hours to control pain. One week later, the cornea was completely healed. After 2 weeks of treatment, the dose was reduced to every 12 hours, and the cornea remained healed after two months of continuous treatment, with no sign of drug toxicity. The patient was then switched to Turbotears™ P2 (0.0025% proparacaine) every 12 hours, as maintenance medication, for 2 additional months. At that time, after four total months of treatment, the cornea remained healed without no evidence of toxicity, and the patient remained pain-free. Turbotears™ P2 was then tapered to once a day as maintenance medication. While the pain was completely controlled, corneal sensation (sensitivity to touch) remained intact throughout the four month course of treatment.

Case B2

Diagnosis: Corneal Abrasion

The patient suffered a corneal abrasion following contact lens use. He was asked to compare Turbotears™ P1 (0.005% proparacaine) and an analgesic solution containing proparacaine 0.01% for the relief of pain. Both drops provided good pain relief. The typical interval between drops for either concentration was 1–2 hours, although occasionally either drop was needed 10–30 minutes apart. Pain subsided and analgesic solutions were discontinued after two days. Examination after four days revealed the cornea completely healed with no evidence of drug toxicity.

Case B3

Diagnosis: Epithelial defect following removal of corneal foreign body

The patient's cornea was drilled to remove a metal foreign body.

After surgery, the patient was given Turbotears™ P1 (0.005% proparacaine) to use as needed for pain. He was comfortable and without pain using the drops every four hours while awake, with epithelial healing occurring in less than 24 hours.

Case B4

Diagnosis: Epithelial defect following removal of corneal foreign body

The patient's cornea was drilled to remove a metal foreign body.

After the surgery, the patient was given Turbotears™ P1 containing 0.005% of proparacaine to use as needed for pain. She was comfortable using the drops every 1–2 hours until bedtime, and had no further pain the next day.

Case B5

Diagnosis: Rosacea

The patient suffered debilitating pain from microscopic corneal epithelial defects in one eye from ocular rosacea.

Turbotears™ P1 (0.005% proparacaine) gave him good relief of pain for several hours after each dose, and he was able to return to work. He was also treated with oral antibiotics for rosacea. Ten days later the cornea was completely healed without any sign of drug toxicity.

Case B6

Diagnosis: Corneal Epithelial Dystrophy

The patient had pain and corneal epithelial defects following anterior stromal puncture, a procedure to treat a corneal epithelial dystrophy. In an office trial, he was given Turbotears™ P2, P3, P4, and P5, containing proparacaine 0.0025%, placebo, 0.001%, and 0.0005% respectively, to compare for the relief of pain. P3 and P5 (0.0005%) had no effect. P4 (0.001%) had a slightly beneficial effect. P2 (0.0025%) provided immediate and significant reduction in pain and sensitivity to light. Therefore, the patient was given P2 (0.0025%) drops to use at home. Good pain relief was achieved by using the drops every 1–3 hours while awake for 5 days. The epithelium healed without evidence of drug toxicity.

Case B7

Diagnosis: Traumatic Corneal Abrasion

The patient was poked in the eye with a toy and presented with corneal abrasion and pain. In an office trial, she was given Turbotears™ T1, T2, T3, T4, and T5, containing tetracaine 0.005%, 0.0025%, placebo, 0.001%, and 0.0005% respectively, to compare for the relief of pain. T4 drops appeared to give some relief of pain, and therefore, the patient was given T4 drops to use at home. However, she returned the next day with significant residual pain despite using the drops every 30 minutes. Therefore, she was given T1 drops (tetracaine 0.005%) to use at home. The patient used the drops every 1–4 hours while awake with good relief of pain. Follow-up examination six days later showed the cornea well-healed with no evidence of drug toxicity.

Case B8

Diagnosis: Traumatic Corneal Abrasion

The patient scratched his cornea with a steel peg. He presented with pain and corneal abrasion. In an office trial, he was given Turbotears™ P2, P3, P4, and P5, containing proparacaine 0.0025%, placebo, 0.001%, and 0.0005% respectively, to compare for the relief of pain. P3 and P5 (0.0005%) had minimal effect. P4 (0.001%) was effective in reducing pain. Therefore, the patient was given P4 (0.001%) drops to use at home. Good pain relief was achieved by using the drops every thirty minutes to nine hours while awake over the next two days. After two days, the cornea was well-healed with no evidence of drug toxicity.

Case B9

Diagnosis: Traumatic Corneal Abrasion

The patient's eye was scratched by a branch and he presented with a small corneal abrasion and moderate pain. In an office trial, he was given Turbotears™ L2, L3, L4, and L5, containing lidocaine 0.0025%, placebo, 0.001%, and 0.0005% respectively, to compare for the relief of pain. L3 (placebo) and L5 (0.0005%) had no significant effect. L4 (0.001%) appeared to make the patient comfortable. The patient reported that he used one drop of L4 that evening to control pain, with immediate relief. The cornea was examined one week later and found to be well-healed with no evidence of drug toxicity.

Case B10

Diagnosis: Traumatic Corneal Abrasion

The patient scratched her cornea with a plant while gardening. She was initially evaluated and patched at another facility. The following day she was referred with persistent severe pain and corneal abrasion. In an office trial, she was given Turbotears™ L1, L2, L3, L4, and L5, containing lidocaine 0.005%, 0.0025%, placebo, 0.001% and 0.0005% respectively, to compare for the relief of pain. L3 (placebo), L4 (0.001%), and L5 (0.0005%) had no significant effect. L2 (0.0025%) appeared to give some pain relief, although the eye still felt uncomfortable. L1 (0.005%) provided significant pain reduction. Therefore, the patient was given L1 (0.005%) drops to use at home. She used the drops every 20 minutes to five hours while awake over the first day, with some foreign body sensation, but the pain was dramatically decreased. The patient, previously debilitated by pain, was able to return to her normal activities. On the second day, only two doses of analgesic solution were needed to control the pain completely. After two days, the cornea was healed with no sign of drug toxicity.

TABLE 2

CLINICAL EVALUATION OF ANALGESIC EFFECT OF LIDOCAINE, PROPARACAINE, AND TETRACAINE

| CASE | DIAGNOSIS | ANESTHETIC | CONCEN-TRATION | REGIMEN | RESULTS |
|---|---|---|---|---|---|
| B1 | Filamentary Keratitis | Proparacaine | 0.005% .0025% | 4 months/ tapered from 2-3 hours to once a day | Good pain relief Healed No toxicity No recurrence |
| B2 | Abrasion | Proparacaine | 0.01% 0.005% | 2 days/every 10 mins. to 2 hours | Good pain relief with .01% and .005%. Healed No toxicity |
| B3 | Epithelial Defect | Proparacaine | 0.005% | 1 day/every 4 hours | Good pain relief Healed |
| B4 | Epithelial Defect | Proparacaine | 0.005% | 1 day/every 1-2 hours | Good pain relief Healed |
| B5 | Ocular Rosacea | Proparacaine | 0.005% | several days few times/day | Good pain relief Healed |
| B6 | Epithelial Dystrophy | Proparacaine | 0.0005% 0.001% 0.0025% hours | — — 5 days/every 1-3 Healed | No effect Slight decrease in pain Good pain relief No toxicity |
| B7 | Abrasion | Tetracaine | 0.0005% 0.001% 0.005% | 1 day/every 30 mins. 2 day/every 1-4 hours | No effect Partial pain relief Good pain relief Healed |
| B8 | Abrasion | Proparacaine | 0.0005% 0.001% | — 2 days/every 30 mins. to 9 hours | Minimal effect Good pain relief Healed |
| B9 | Abrasion | Lidocaine | 0.0005% 0.001% | — 1 day/1 dose | No effect "Instant" pain relief Healed |
| B10 | Abrasion | Lidocaine | 0.0005% 0.001% 0.0025% 0.005% | — — — 2 days/every 20 mins. to 5 hours | No effect No effect Partial pain relief Good pain relief Healed |

In summary, in ten patients with corneal epithelial defects, dilute solutions of lidocaine, proparacaine, and tetracaine provided sustained analgesia when applied repeatedly as eye drops. There was no delay in epithelial healing. No toxic effects were noted after as long as 4 months of treatment.

EXAMPLE 3

Clinical Study (C) of Sustained Analgesia Effects of Ultralow Concentrations of Local Anesthetics This example illustrates clinical experiments and evaluation of 25 patients (C1-C25) receiving various ophthalmic analgesic solutions of various concentrations.

This example includes four types of corneal epithelial defects not presented in Examples 1 and 2. Dry eye causes microerosions of the corneal epithelium, with chronic pain. Corneal edema causes swelling of the epithelial cells, with resultant pressure on nerve endings and micro and macro epithelial erosions or defects. In pterygium surgery and photorefractive keratectomy (PRK), the surface epithelium and anterior stromal layer of the cornea are removed, creating epithelial defects which heal over several days.

Solutions

Benoxinate hydrochloride was obtained from Barnes Hind Pharmaceuticals in a 0.4% solution as the anesthetic agent in Fluoress®, a 0.25% fluorescein solution.

Bupivacaine hydrochloride, preservative free, known under its trade name SENSORCAINE-MPF®, was obtained from Astra Pharmaceutical Products as 0.5% solution for injection.

Proparacaine hydrochloride, known under its trade name ALCAINE®, was obtained from Alcon Laboratories, Fort Worth, Tex., as 0.5% ophthalmic solution.

Tetracaine hydrochloride was obtained from Iolab Corporation as 0.5% ophthalmic solution.

Using a tuberculin syringe and a 30 g needle to allow accurate dilution with HYPOTEARS®, a commercially available artificial tear preparation from Iolab Corporation, solutions of benoxinate, bupivacaine, proparacaine, and tetracaine were prepared at various concentrations. These solutions were given the generic name "Turbotears™" and were designated as follows:

| Turbotears ™ | |
|---|---|
| B1 | Benoxinate 0.005% (50 µg/ml) in artificial tears |
| B2 | Benoxinate 0.0025% (25 µg/ml) in artificial tears |
| B3 | Artificial tears |
| B4 | Benoxinate .001% (10 µg/ml) in artificial tears |
| B5 | Benoxinate .0005% (5 µg/ml) in artificial tears |

-continued

| Turbotears ™ | |
|---|---|
| B.01% | Benoxinate .01% (100 µg/l) in artificial tears |
| B.02% | Benoxinate .02% (200 µg/l) in artificial tears |
| BU1 | Bupivacaine 0.005% (50 µg/ml) in artificial tears |
| BU2 | Bupivacaine 0.0025% (25 µg/ml) in artificial tears |
| BU.01% | Bupivacaine 0.01% (100 µg/ml) in artificial tears |
| BU.05% | Bupivacaine 0.05% (500 µg/ml) in artificial tears |
| P1 | Proparacaine 0.005% (50 µg/ml) in artificial tears |
| P2 | Proparacaine 0.0025% (25 µg/ml) in artificial tears |
| P3 | Artificial tears |
| P4 | Proparacaine 0.001% (10 µg/ml) in artificial tears |
| P5 | Proparacaine 0.0005% (5 µg/ml) in artificial tears |
| P.01% | Proparacaine 0.01% (100 µg/ml) in artificial tears |
| P.02% | Proparacaine 0.02% (200 µg/ml) in artificial tears |
| P.03% | Proparacaine 0.03% (300 µg/ml) in artificial tears |
| P.05% | Proparacaine 0.05% (500 µg/ml) in artificial tears |
| T1 | Tetracaine 0.005% (50 µg/ml) in artificial tears |
| T2 | Tetracaine 0.0025% (25 µg/ml) in artificial tears |
| T3 | Artificial tears |
| T4 | Tetracaine 0.001% (10 µg/ml) in artificial tears |

The following patients were treated to test the safety and efficacy of these Turbotears™ solutions:

Case C1

Diagnosis: Corneal Abrasion

The patient suffered a corneal abrasion following contact lens use. In an office trial, Turbotears™ B5, B4 and B3 had no significant analgesic effect. Turbotears™ B2 (0.0025% benoxinate) and B1 (0.005% benoxinate) gave progressively greater pain relief. The patient used the latter solution 31 times over the next two days, typically every 10–30 minutes while awake. Pain was controlled and the epithelium was well-healed by day 3, without evidence of toxicity.

Case C2

Diagnosis: Corneal Abrasion

The patient awoke with pain and corneal abrasion. Turbotears B2 (0.0025% benoxinate) and B0.01% (0.01% benoxinate) gave only slight pain relief in an office trial. Higher concentrations were not tried.

Case C3

Diagnosis: Traumatic Corneal Abrasion

The patient suffered corneal abrasion when hit in the left eye with a toy. In an office trial, Turbotears™ B3 (artificial tears) gave no relief of pain. Turbotears™ B5 (0.0005% benoxinate) had only slight analgesic effect. Turbotears™ B4 (0.001% benoxinate) and B2 (0.0025% benoxinate) were more effective, subjectively reducing pain 50%. Turbotears™ B1 (0.005% benoxinate) reduced pain 80%, and was therefore used 11 times over the next 5 hours with good pain relief. However, that night the patient's pain persisted, and therefore he was given Turbotears™ B0.01% (0.01% benoxinate). He had immediate pain relief and was able to sleep. He used 3 doses the next morning over 2 hours and he had no further pain. The cornea healed without delay or toxicity.

Case C4

Diagnosis: Traumatic Corneal Abrasion

A piece of paper scratched the patient's right cornea. Patching was not tolerated. Turbotears™ B3 (artificial tears) had no effect. Turbotears B5 (benoxinate 0.0005%) provided partial pain relief. Both B4 (benoxinate 0.001%) and B2 (benoxinate 0.0025%) eliminated her pain. The patient used Turbotears™ B2 every 1 to 3 hours that day and once the following morning. She had good pain relief, and the cornea was completely healed when examined 3 days later.

Case C5

Diagnosis: Traumatic Corneal Abrasion

A tree branch scratched the patient's right cornea. Turbotears™ B0.01% (benoxinate 0.01%) was used every ½ hour for about 6 hours, but only relieved the pain for the first hour. Therefore, B0.02% (benoxinate 0.02%) was substituted. Application every ½ hour provided good analgesia for the rest of the day.

The drops were used once the following morning, and the patient had no further pain. His cornea healed without sequelae.

Case C6

Diagnosis: Epithelial Defect Following Removal of Corneal Foreign Body

The patient's cornea was drilled to remove a metal foreign-body.

After the surgery, the patient was given Turbotears™ B3 (artificial tears), B1 (0.005% benoxinate) and B2 (0.0025% benoxinate). B3 was of no benefit. B1 and B2 gave equal analgesic effect, used every 10 minutes to 2 hours the first day. The drops were used 3 times on day 2, once on day 3, and the patient was pain-free on day 4.

Case 7

Diagnosis: Traumatic Corneal Abrasion

The patient was hit in the left eye with a dog biscuit and suffered corneal abrasion. Turbotears™ B1 (0.005% benoxinate) was the lowest concentration that gave satisfactory pain relief. She used the drops 16 times on day 1, 11 times on day 2, and twice on days 3 and 4. The cornea was well-healed when examined on day 9.

Case C8

Diagnosis: Traumatic Corneal Abrasion

The patient was kicked in the left eye by a 2 year old child. He was seen with persistent corneal abrasion and pain after 2 days of patching and vicodin (narcotic oral pain medication). Turbotears™ BU1 (0.005% bupivacaine) and BU2 (0.0025% bupivacaine) had limited analgesic effect. Turbotears™ BU0.01% (0.01% bupivacaine) and BU0.05% (0.05% bupivacaine) gave progressively greater analgesic effect. The patient used Turbotears™ BU0.05% 15 times in the next 24 hours, with good pain relief. He was also treated with a bandage contact lens and antibiotic drops. His cornea healed without toxic effects.

Case C9

Diagnosis: Traumatic Corneal Abrasion

The patient was initially treated elsewhere with antibiotic and patch for a traumatic corneal abrasion (a finger poked his right eye). The following day the patient had significant pain and photophobia with partial healing of the epithelium. Patching was discontinued, and the patient used Turbotears™ P0.05% (0.05% proparacaine) every 45–60 minutes for the next 12 hours with excellent relief of pain. He was pleased because he could open his eye and work. The patient was pain-free and the cornea well-healed by the following day.

Case C10

Diagnosis: Surgical Corneal Abrasion for Map Dot Fingerprint Corneal Dystrophy

The patient's corneal epithelium was removed for treatment of a dystrophy, using conventional topical anesthetic. Pain was controlled in the first 24 hours with patch and oral pain medication. In a office trial, Turbotears™ P3 (artificial tears) had no effect. Turbotears™ P1 (0.005% proparacaine) provided significant analgesia. Comfort was maintained with 6 drops on day 1, 2 drops on day 2, and 1 drop on day 3. The epithelial defect was healed when the patient was examined on day 4. One month later the cornea was clear with 20/20 vision.

Case C11

Diagnosis: Traumatic Corneal Abrasion

The patient suffered a corneal abrasion when a dog scratched her left eye. She used Turbotears™ P0.05% (proparacaine 0.05%) every 1 to 5 hours while awake over the next 2 days. The drops reduced her pain and allowed her to open her eye. The cornea was well-healed without toxicity when examined 4 days later.

Case C12

Diagnosis: Epithelial Defect Secondary to Map Dot Fingerprint Dystrophy

The patient developed a large corneal epithelial defect secondary to map dot fingerprint corneal dystrophy. He used Turbotears™ P0.01% (proparacaine 0.01%) 1 to 2 times per day over the next 3 days. He claimed the drops gave him sustained and substantial pain relief. The abrasion was well-healed when checked 6 days later.

Case C13

Diagnosis: Corneal Abrasion With Map Dot Fingerprint Corneal Dystrophy

The patient suffered corneal abrasion secondary to corneal dystrophy. She was given Turbotears™ P0.05% (0.05% proparacaine). She used the drops 14 times from 2 p.m. to 10 p.m. Pain was controlled, but she noticed progressive conjunctival and eyelid swelling. The pain was much less the following day, and therefore the Turbotears™ were discontinued, as the redness and swelling concerned the patient. Despite what was probably an allergic reaction, the cornea was well-healed without evidence of toxicity when examined on day 5.

Case C14

Diagnosis: Corneal Epithelial Edema

The patient developed corneal epithelial swelling or edema after the vitreous gel contacted the endothelium, or inner "pump" layer of the cornea, following eye surgery. This epithelial edema caused chronic pain and photophobia (light sensitivity). The patient was given Turbotears™ P0.02% (0.02% proparacaine). Over the next 17 days, the patient achieved good pain relief using 93 doses of Turbotears™, sometimes as often as 15 minutes apart. The corneal edema resolved with further eye surgery, and no toxic effects on the epithelium were seen.

Case C15

Diagnosis: Micro-epithelial Defects Secondary to Dry Eyes

Insufficient tears led to microscopic erosions, or defects, of the corneal epithelium, with chronic pain and redness. Artificial tears did not relieve her symptoms. The patient used Turbotears™ P0.02% (0.02% proparacaine) 2 to 4 times per day over the next 2 weeks. She was happy and pleasantly surprised with decreased redness and no pain. There was no evidence of corneal toxicity.

Case 16

Diagnosis: Corneal Epithelial Defect Following Pterygium Surgery

One day after pterygium surgery, the patient had a large residual epithelial defect. She was nauseated from oral pain medication.

In an office trial, Turbotears™ P0.03% (0.03% proparacaine) were the minimal strength to relieve her pain. The drops provided analgesia for about 15 minutes when she had pain at night. She used 15 doses over the next 2 days, when her cornea was seen to be healed without toxicity.

Case C17

Diagnosis: Corneal Epithelial Defect Following Pterygium Surgery

One day after pterygium surgery, the patient had a moderate-sized residual epithelial defect. He used Turbotears™ P0.05% (proparacaine 0.05%) every 1 to 3 hours while awake for the next 5 days. Pain was significantly reduced by the drops. The cornea healed without evidence of toxicity.

Cases 18–24

Diagnosis: Corneal Epithelial Defect Following Photorefractive Keratectomy (PRK)

Photorefractive keratectomy (PRK) is a laser procedure in which the corneal surface is reshaped to correct nearsightedness (myopia). The resulting corneal epithelial defect usually heals in 3–4 days.

A pilot analgesia study performed in April 1993 indicated that Turbotears™ P0.01% (0.01% proparacaine) was ineffective in providing significant analgesia for post-op PRK patients. In the same study proparacaine 0.03% seemed to be effective. Turbotears™ concentrations were selected for the following 7 patients based on this pilot study.

These 7 patients underwent PRK for correction of myopia. All 7 were fit with bandage soft contact lenses post-operatively to promote comfort and epithelial healing. However, all 7 experienced significant post-operative pain not relieved by voltaren drops. One patient was given Turbotears™ P0.03% (0.03% proparacaine). Four patients were given Turbotears™ P0.05% (0.05% proparacaine). Two patients were given both P0.05% and BU0.05% (bupivacaine 0.05%). All seven patients had significant pain relief with each of their respective Turbotears™ solutions, used for 1 to 3 days. No corneal toxicity was seen.

Case C25

Diagnosis: Traumatic Corneal Abrasion

The patient suffered a corneal abrasion when debris from a bush flew into his eye. The following Turbotears™ solution were tried in the office: T3 (artificial tears) had no analgesic effect. T1 (0.005% tetracaine) and T2 (0.0025% tetracaine) provided significant pain relief, compared to the minimal effect of T4 (0.001% tetracaine). The patient use Turbotears™ T1 every 30 minutes to 2 hours that afternoon and the next morning. He noted good pain relief for 15 minutes, followed by slow return of pain. The abrasion was healed when examined 4 days later.

TABLE 3

CLINICAL EVALUATION OF ANALGESIC EFFECT OF BENOXINATE, BUPIVACAINE, PROPARACAINE AND TETRACAINE

| CASE | DIAGNOSIS | ANESTHETIC | CONCENTRATION | REGIMEN | RESULTS |
|---|---|---|---|---|---|
| C1 | Abrasion | Benoxinate | 0.005% | 3 days/ 10–30 min for 2 days | Good pain relief Healed No toxicity |
| C2 | Abrasion | Benoxinate | 0.01% 0.0025% | 1 time 1 time | Only slight analgesic effect |
| C3 | Abrasion | Benoxinate | 0.0005% 0.0025% 0.005% 0.01% | 2 days/ 11 times in 5 hours At bedtime | Slight pain relief 50% pain relief Comfortable until night Good pain relief Healed No toxicity |
| C4 | Abrasion | Benoxinate | 0.0005% 0.001% 0.0025% | 2 days every 1–3 hours | Partial pain relief Good pain relief Healed No toxicity |
| C5 | Abrasion | Benoxinate | 0.01% 0.02% | 1 day/every 30 mins. for 6 hours | Pain relief for first hour Good pain relief Healed No toxicity |
| C6 | Abrasion | Benoxinate | 0.0025% 0.005% | 3 days/every 10 mins. to 2 hrs. on day 1, 3× on day 2, and 1× on day 3 | Good pain relief Healed No toxicity |
| C7 | Abrasion | Benoxinate | 0.005% | 4 days/ 16× on day 1/ 11× on day 2/ 2× on days 3 & 4 | Good pain relief Healed No toxicity |
| C8 | Abrasion | Bupivacaine | 0.0025% 0.005% 0.05% | 1 day/15× | Limited pain relief Limited pain relief Good pain relief Healed No toxicity |
| C9 | Abrasion | Proparacaine | 0.05% | 1 day/ every 45–60 minutes | Good pain relief Healed No toxicity |
| C10 | Abrasion | Proparacaine | 0.005% | 4 days/up to 6 times per day | Good pain relief Healed No toxicity |
| C11 | Abrasion | Proparacaine | 0.05% | 2 days/every 1–5 hrs. for 2 days | Pain reduced Healed No toxicity |
| C12 | Epithelial Dystrophy | Proparacaine | 0.01% | 3 days/1–2× per day | Sustained pain relief Healed No toxicity |
| C13 | Epithelial Dystrophy | Proparacaine | 0.05% | 1 day/ 14× over 8 hrs. | Pain controlled Eyelid swelling, conjunctiva red decreased Cornea healed No corneal toxicity |
| C14 | Corneal edema | Proparacaine | 0.02% | 17 days/93 doses/ 15 mins | Good pain relief No toxicity |
| C15 | Dry eyes | Proparacaine | 0.02% | 2 weeks/2–4× per day | Good pain relief Less redness |
| C16 | Post-op pterygium | Proparacaine | 0.03% | 2 days/15× | Good pain relief Healed No toxicity |
| C17 | Post-op pterygium | Proparacaine | 0.05% | 5 days/every 1–3 hrs. | Pain reduced Healed No toxicity |
| C18–24 | Post-op PRK | Proparacaine Bupivacaine | 0.03% 0.05% 0.05% | 1–3 days/as needed | Good pain relief All healed No toxicity |
| C25 | Abrasion | Tetracaine | 0.001% 0.0025% 0.005% | 4 days/ every 30 mins to 2 hours | Minimal effect Good pain relief Healed No toxicity |

EXAMPLE 4

Subanesthetic Concentrations of Local Anesthetics for Topical Corneal Analgesia This example demonstrates that the ultralow concentrations of local anesthetics used on corneal epithelial defects for analgesia are subanesthetic concentrations of the local anesthetics.

A Luneau anesthesiometer was used to quantify corneal sensation after application of ultralow concentrations of proparacaine. The instrument was calibrated from 0 to 6, with 0 indicating complete absence of corneal sensation, and 6 indicating the greatest sensitivity to touch.

Controls

Three normal volunteers were used as controls. One eye was tested in each of three volunteers. The sequence of drops applied to the eye was: placebo (Hypotears), proparacaine 0.005%, 0.01%, 0.03%, 0.05% and 0.5% Corneal sensation was tested on minute after each drop was applied. The respective anesthesiometer readings were 5 (placebo), 5 (proparacaine 0.005%), 5 (proparacaine 0.01%), 5 (proparacaine 0.03%), 4 (proparacaine 0.05%), and 0 (proparacaine 0.5% anesthetic concentration) (normal eye 1); 3.5 (placebo), 3.5 (proparacaine 0.005%), 4.0 (proparacaine 0.01%); 3.0 (proparacaine 0.03%), 3.0 (proparacaine 0.05%) and 0 (normal eye 2); and 5 (placebo), 5 (proparacaine 0.005%), 5 (proparacaine 0.01%), 4.5 (proparacaine 0.03%), 4.5 (proparacaine 0.05%) and 0 (proparacaine 0.5%) (normal eye 3).

Case 1—Corneal Abrasion

One patient with a painful corneal abrasion was given proparacaine 0.05% with good pain relief. Anesthesiometer reading after a single drop was 4.

Case 2—Keratitis

A 75 year old lady with painful keratitis (inflammation of the cornea) of the left eye was given the same series of proparacaine drops in the left eye as noted above. Anesthesiometer readings were 5 (placebo), 5 (proparacaine 0.005%), 4.5 (proparacaine 0.01%), 4.0 (proparacaine 0.03%), 3.0 (proparacaine 0.03%), and 0 (proparacaine 0.5%).

Case 3—Corneal Abrasion

A 45 year old firefighter with painful bilateral corneal erosions was given the same series of drops in each eye. His anesthesiometer readings were 4.0 (placebo), 5.0 (proparacaine 0.005%), 4.5 (proparacaine 0.01%), 4.5 (proparacaine 0.03%), 5.0 (proparacaine 0.05%), and 0 (proparacaine 0.5%) (right eye); and 6.0 (placebo), 5.0 (proparacaine 0.005%), 5.5 (proparacaine 0.01%), 5.0 (proparacaine 0.03%), 4.5 (proparacaine 0.05%), and 0 (proparacaine 0.5%) (left eye).

In summary, in all cases when ultralow subanesthetic concentrations of proparacaine were administered, corneal sensation was present, but was absent when the anesthetic concentration (0.5%) of proparacaine was applied. The results observed for this group of 6 patients are compiled in Table 4.

TABLE 4

| PATIENT | Anesthesiometer Readings | | | | | |
|---|---|---|---|---|---|---|
| | 0.000% | 0.005% | 0.01% | 0.03% | 0.05% | 0.5% |
| 1. Normal eye | 5 | 5 | 5 | 5 | 4 | 0 |
| 2. Normal eye | 3.5 | 3.5 | 4.0 | 3.0 | 3.0 | 0 |
| 3. Normal eye | 5 | 5 | 5 | 4.5 | 4.5 | 0 |
| 4. Corneal Abrasion | — | — | — | — | 4 | — |
| 5. Keratitis | 5 | 5 | 4.5 | 4.0 | 3.0 | 0 |
| 6. Corneal Erosions | | | | | | |
| Right | 4 | 5 | 4.5 | 4.5 | 5 | 0 |
| Left | 6 | 5 | 5.5 | 5.0 | 4.5 | 0 |

When an anesthetic concentration (0.5% and above) of the anesthetic was administered to the eye, anesthesia of the cornea occurred, evidenced by the complete loss of touch sensation. On the other hand, when ultralow subanesthetic concentrations (0.05% and below) of local anesthetic were applied to the cornea, analgesia was achieved without loss of corneal touch sensation, that is, without inducing corneal anesthesia. Subanesthetic concentrations of the local anesthetics produced an analgesic effect when applied topically to the cornea.

What is claimed is:

1. An in vivo method for safe, extended and sustained corneal analgesia in a human patient without corneal toxicity and without loss of the cornea's protective touch sensation, comprising topical administration to the patient's cornea of an ophthalmic analgesic solution containing a subanesthetic concentration of local anesthetic from about 0.001% to about 0.05%.

2. The method of claim 1 wherein the local anesthetic is selected from the group consisting of proparacaine, tetracaine, lidocaine, procaine, hexylcaine, cocaine, bupivacaine, benoxinate, mepivacaine, prilocaine, etidocaine, benzocaine, chloroprocaine, propoxycaine, dyclonine, dibucaine, and pramoxine.

3. The method of claim 2 wherein the local anesthetic is proparacaine, lidocaine, tetracaine, benoxinate or bupivacaine.

4. The method of claim 3 wherein the concentration of anesthetic in the solution is about 0.001%.

5. The method of claim 3 wherein the concentration of anesthetic in the solution is about 0.0025%.

6. The method of claim 3 wherein the concentration of anesthetic in the solution is about 0.005%.

7. The method of claim 3 wherein the concentration of anesthetic in the solution is about 0.01%.

8. The method of claim 3 wherein the concentration of anesthetic in the solution is about 0.05%.

9. The method of claim 3 wherein the anesthetic is proparacaine administered as often and for as long as needed.

10. An in vivo method for safe, extended and sustained corneal analgesia in a human patient without corneal toxicity and loss of cornea's protective touch sensation, comprising topical administration to the patient's cornea of an ophthalmic analgesic preparation containing a subanesthetic concentration of local anesthetic from about 0.001% to about 0.05%.

11. The method of claim 10 wherein the ophthalmic analgesic preparation is an ointment, cream, gel, or sustained release vehicle.

12. The method of claim 11 wherein the local anesthetic is selected from the group consisting of proparacaine, tetracaine, lidocaine, procaine, hexylcaine, cocaine, bupivacaine, benoxinate, mepivacaine, prilocaine, etidocaine, benzocaine, chloroprocaine, propoxycaine, dyclonine, dibucaine, and pramoxine.

13. The method of claim 12 wherein the anesthetic is proparacaine, tetracaine, lidocaine, benoxinate, or bupivacaine administered as often and for as long as needed.

14. The method of claim 13 wherein the concentration of anesthetic in the preparation is about 0.001%.

15. The method of claim 13 wherein the concentration of anesthetic in the preparation is about 0.0025%.

16. The method of claim 13 wherein the concentration of anesthetic in the preparation is about 0.005%.

17. The method of claim 13 wherein the concentration of anesthetic in the preparation is about 0.01%.

18. The method of claim 13 wherein the concentration of anesthetic in the preparation is about 0.05%.

19. An in vivo method for safe, extended and sustained corneal analgesia in a human patient without corneal toxicity and without loss of cornea's protective touch sensation comprising steps:
   (a) preparing a topical ophthalmic analgesic solution containing a subanesthetic concentration of local anesthetic from about 0.001% to about 0.05%;
   (b) topically administering about 1–3 drops of the solution of step (a) to the patient requiring corneal analgesia;
   (c) repeating the administration of the ophthalmic solution of step (b) as often and for as long as needed.

20. The method of claim 19 wherein the local anesthetic is selected from the group consisting of proparacaine, tetracaine, lidocaine, procaine, hexylcaine, cocaine, bupivacaine, benoxinate, mepivacaine, prilocaine, etidocaine, benzocaine, chloroprocaine, propoxycaine, dyclonine, dibucaine, and pramoxine.

21. The method of claim 20 wherein the anesthetic is proparacaine, lidocaine, tetracaine, benoxinate or bupivacaine.

22. The method of claim 21 wherein the concentration of anesthetic in the preparation is about 0.001%.

23. The method of claim 21 wherein the concentration of anesthetic in the preparation is about 0.0025%.

24. The method of claim 21 wherein the concentration of anesthetic in the preparation is about 0.005%.

25. The method of claim 21 wherein the concentration of anesthetic in the preparation is about 0.01%.

26. The method of claim 21 wherein the concentration of anesthetic in the preparation is about 0.05%.

27. A topical ophthalmic analgesic solution consisting essentially of from about 0.001% to about 0.05% of local anesthetic selected from the group consisting of proparacaine, tetracaine, lidocaine, benoxinate and bupivacaine dissolved in an artificial tear solution or sterile purified water containing pharmaceutically acceptable excipients, additives or preservatives.

28. The solution of claim 27 wherein the anesthetic is proparacaine.

29. The solution of claim 27 wherein the anesthetic is lidocaine.

30. The solution of claim 27 wherein the anesthetic is tetracaine.

31. The solution of claim 27 wherein the anesthetic is benoxinate.

32. The solution of claim 27 wherein the anesthetic is bupivacaine.

* * * * *